(12) United States Patent
Boomgaarden (10) Patent No.: US 7,841,030 B2
(45) Date of Patent: Nov. 30, 2010

(54) POSITIONING SYSTEMS AND METHODS

(75) Inventor: Jonathan Carl Boomgaarden, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 219 days.

(21) Appl. No.: 12/128,435

(22) Filed: May 28, 2008

(65) Prior Publication Data

US 2009/0293196 A1 Dec. 3, 2009

(51) Int. Cl.
*A61B 19/00* (2006.01)
(52) U.S. Cl. .................................. 5/608; 5/601; 5/600
(58) Field of Classification Search .............. 5/600–601, 5/607–610
See application file for complete search history.

(56) References Cited

U.S. PATENT DOCUMENTS

| | | | |
|---|---|---|---|
| 2,692,173 A * | 10/1954 | Lowitzsch | ..................... 5/601 |
| 4,013,019 A | 3/1977 | Horsey | |
| 4,589,642 A | 5/1986 | Schnelle et al. | |
| 4,672,697 A | 6/1987 | Schurch | |
| 5,237,600 A | 8/1993 | Kamata | |
| 5,368,113 A | 11/1994 | Schulze-Beckinghausen | |
| 5,490,296 A | 2/1996 | Fleury et al. | |
| 5,490,297 A | 2/1996 | Bradcovich et al. | |
| 5,561,699 A | 10/1996 | Fenner | |
| 5,791,233 A | 8/1998 | Knapp et al. | |
| 5,829,076 A | 11/1998 | Csikos et al. | |
| 6,109,424 A | 8/2000 | Doan | |
| 6,244,745 B1 | 6/2001 | Mattern | |
| 6,322,472 B1 | 11/2001 | Schulze-Beckinghausen | |
| 6,375,355 B1 | 4/2002 | Fortin | |
| 6,382,832 B1 | 5/2002 | Schwieker et al. | |
| 6,615,429 B2 | 9/2003 | Weil et al. | |
| 6,681,423 B2 | 1/2004 | Zachrisson | |
| 6,769,145 B1 | 8/2004 | Pfeuffer et al. | |
| 6,886,200 B2 | 5/2005 | Blyshak et al. | |
| 7,000,271 B2 | 2/2006 | Varadharajulu | |
| 7,168,854 B2 | 1/2007 | Ergun et al. | |
| 7,270,619 B2 | 9/2007 | Bourc'His | |
| 2004/0068797 A1 | 4/2004 | Smith et al. | |

OTHER PUBLICATIONS

Serapid S.A.; www.serapid.com; "Rigid-Chain Technology for Vertical Movement"; First Edition, Revision C; Serapid May 2005; 24 pages.
Serapid S.A.; www.serapid.com; "A Chain That Pulls and Pushes Can Do the Lifting As Well"; 4 pages.

* cited by examiner

*Primary Examiner*—Fredrick Conley
(74) *Attorney, Agent, or Firm*—Dean D. Small; Small Patent Law Group (57) ABSTRACT

A positioning system configured to move a patient or support into position or in a guided manner. The system includes a table that is configured to hold the patient or object and a column that is coupled to the table. The column is configured to support and move the table and includes a plurality of links pivotably coupled to each other in series. Adjacent links are configured to pivot in only one direction from a linear stacked arrangement. The system also includes a guide that is configured to receive and direct the links of the column into the linear stacked arrangement when the links are moved by a lifting force along the guide.

20 Claims, 10 Drawing Sheets

POSITIONING SYSTEMS AND METHODS

BACKGROUND OF THE INVENTION

This invention relates generally to positioning systems, and more particularly to systems for holding a load, such as a patient, in position or for moving the load in a guided manner.

Many industries use positioning systems to raise and hold large loads for a predetermined period of time or guide the large loads along a path. For instance, in the medical industry patients must be raised and held in a predetermined position so that a surgeon may operate on the patient or so that a technician may acquire an image of the patient. When taking medical images of a patient, such as by radiographic or fluoroscopic imaging, the patient must remain in a predetermined position or moved along a predetermined path while the image or images are being acquired. The positioning system may use, for example, a table that starts from a lowered position where the patient can initially sit or lie down on the table and then moves to a raised position within the imaging field.

However, conventional positioning systems have limited movement capabilities and/or load capacities. For example, some known positioning systems include scissor mechanisms that lift the table from the floor to the raised position. The positioning systems that use scissor mechanisms are generally limited to vertical movement and allow little, if any rotational or lateral movement when the scissor mechanisms are fully extended. In addition, the scissor mechanisms are generally located along sides of the table, which may limit access to the table or movement of an imaging device around the table. Also, the scissor mechanisms typically provide a carving mechanical advantage that may require a more complex method of providing power to the scissor mechanism in order for the movement to be constant. Other known positioning systems use multi-stage lifts/pedestals or poles to move the table. However, like the positioning systems that use scissor mechanisms, the multi-stage systems have limited movement capabilities and load capacities.

Thus, there is a need for positioning systems that allow for greater movement capabilities and load capacities than known positioning systems. Also, there is a need for positioning systems that use a reduced amount of space under the table or support. Further, there is a need for positioning systems that provide a substantially constant mechanical advantage.

BRIEF DESCRIPTION OF THE INVENTION

In one embodiment, a positioning system configured to move a patient into position or in a guided manner is provided. The system includes a table that is configured to hold the patient and a column that is coupled to the table. The column is configured to support and move the table and includes a plurality of links pivotably coupled to each other in series. Adjacent links are configured to pivot in only one direction from a linear stacked arrangement. The system also includes a guide that is configured to receive and direct the links of the column into the linear stacked arrangement when the links are moved by a lifting force along the guide.

Optionally, the positioning system may include a driving mechanism that is operatively coupled to the column and configured to move the column along the guide. Also, the positioning system may include a rotation system that is coupled to the table and the column where the rotation system is configured to rotate the table about a rotation axis. Furthermore, the adjacent links may be coupled to one another along a fold axis and may be configured to rotate about the fold axis between the stacked linear arrangement and a flexed arrangement.

Also optionally the positioning system may include a bias chain coupled to and extending between a leading end and a back end of the column. The bias chain is configured to maintain the links of the column in a linear arrangement when the column is not being redirected by the guide.

In another embodiment a method for moving a patient into position or in a guided manner is provided. The method includes coupling a column to a table that is configured to hold the patient. The column is configured to support and move the table when a lifting force is applied. The column also includes a plurality of links that are pivotably coupled to each other in series. The adjacent links are configured to pivot in only one direction from a linear stacked arrangement. The method also includes moving the column along a guide configured to receive and direct the links of the column. The guide is configured to direct the links into the linear stacked arrangement when the links are moved by the lifting force.

In another embodiment, a method for moving a support into position or in a guided manner is provided. The method includes coupling the support to an end of a flexible column. The column includes a plurality of links coupled to one another. The links form a linear lift extension and a reserve extension. The lift extension is configured to support the table and extend in a load direction, and the reserve extension has at least a portion that extends in a non-load direction. The method also includes coupling the support to a rotation system that is configured to rotate the support about a rotation axis proximate to the end of the column. The method further includes moving the column along a guide configured to receive the links as the column is moved in the load direction. The guide redirects the links such that links received from the reserve extension are added to the lift extension.

DETAILED DESCRIPTION OF THE INVENTION

As used herein, an element or step recited in the singular and proceeded with the word "a" or "an" should be understood as not excluding plural of said elements or steps, unless such exclusion is explicitly stated. "Patient" and individual, as used herein, may include not only humans but also animals.

Furthermore, references to "one embodiment" of the present invention are not intended to be interpreted as excluding the existence of additional embodiments that also incorporate the recited features. Moreover, unless explicitly stated to the contrary embodiments "comprising" or "having" or "including" an element or a plurality of elements having a particular property may include additional such elements not having that property.

Figure 1:
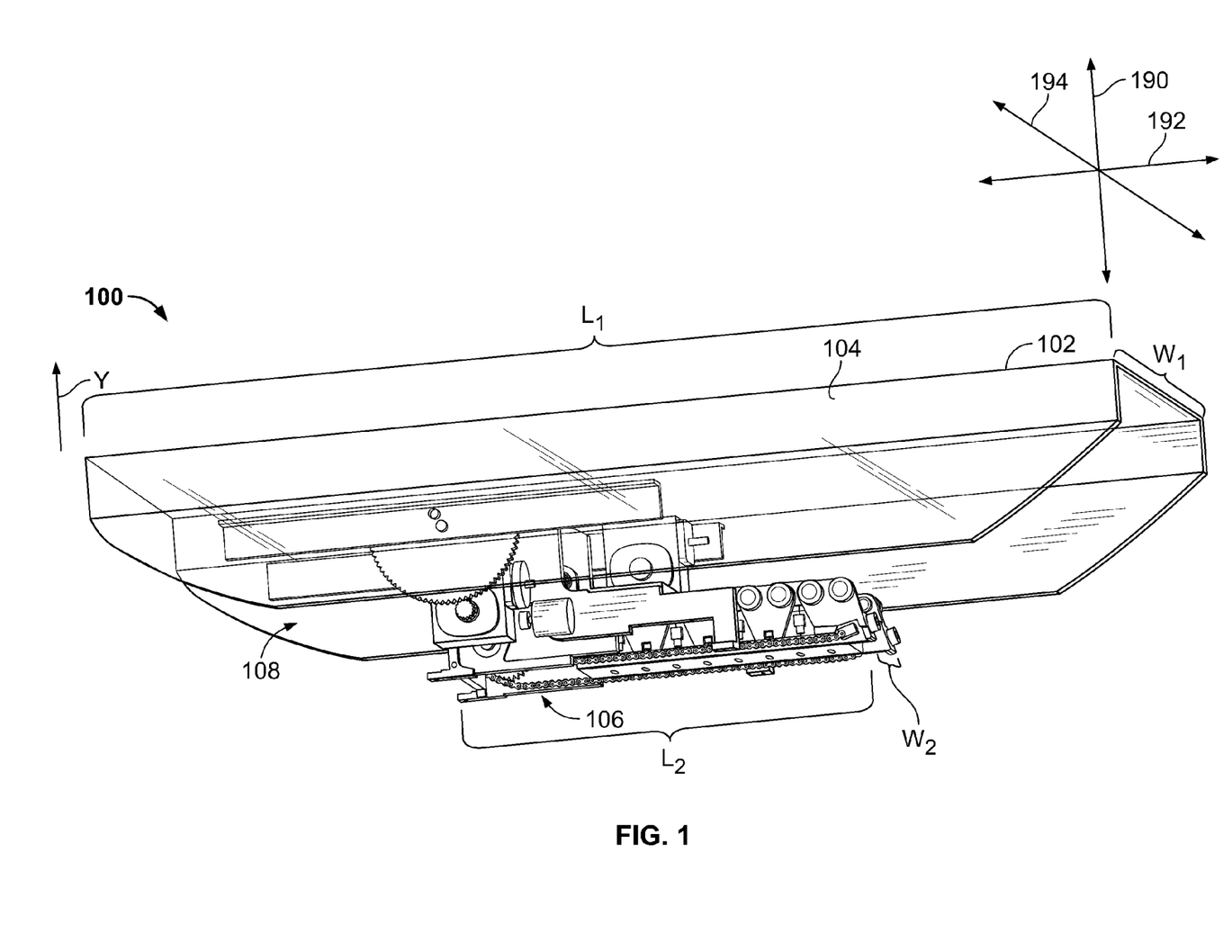
FIG. 1 is a perspective view of a positioning system formed in accordance with one embodiment.

FIG. 1 is a perspective view of a positioning system 100 formed in accordance with one embodiment. The positioning system 100 includes a support 102 that is directly or indirectly coupled to an elevation system 106 and a rotation system 108. In the exemplary embodiment, the support 102 is a table 104 that is configured to hold a load, such as an individual or patient during a medical examination, operation, or imaging session. However, the support 102 may take other forms and shapes in alternative embodiments. FIG. 1 shows the positioning system 100 having the support 102 in a fully retracted or lowered position. As will be discussed in greater detail below, the elevation system 106 and the rotation system 108 include various parts and mechanisms for moving the support 102 in a linear lift or load direction (indicated by an arrow Y) along a vertical axis 190 or for rotating or tilting the support 102 about a rotational axis that is parallel to a lateral axis 194. In some embodiments, the positioning system 100 may also include a translating or sliding system (not shown) for moving the support 102 in a linear direction along a longitudinal axis 192. The elevation and rotation systems 106 and 108 (and optionally the translating system) may be communicatively coupled to a control system (not shown) that may be operated automatically or operated by a technician for selecting a desired position for the support 102 or movement thereof. Alternatively, the positioning system 100 may be manually or mechanically operated by a person.

By way of one example the positioning system 100 may be operated to move a patient into predetermined positions or move the patient along predetermined paths during a radiographic (x-ray) or a fluoroscopic imaging session. However, although embodiments of the positioning system 100 discussed herein are described as being used for medical purposes, alternative embodiments may be used in other applications. In addition to patients or individuals, for example, the positioning system 100 may be configured to hold objects in predetermined positions or move the objects along predetermined paths. For example, the positioning system 100 may be used for moving a stage or platform to a raised level, or the positioning system 100 may be used for holding automobile parts and frames while an automobile is being assembled. As such, the different parts and components of the positioning system 100 may be configured for different purposes. For example, the support 102 may be a pallet or skid, a pair of parallel rails, or the support 102 may have any other shape that is configured to hold an object in a desired orientation.

Also shown in FIG. 1, the support 102 has a length $L_1$ that extends along the axis 192 and a width $W_1$ that extends along the axis 194. In one embodiment, the elevation system 106 has a length $L_2$ and a width $W_2$ that are substantially shorter than the length $L_1$ and the width $W_1$, respectively, of the support 102. For example, the length $L_1$ and the width $W_1$ of the support 102 may be approximately 1.5 to 2.0 meters and approximately 0.75 to 1.0 meters, respectively. The width $W_2$ of the elevation system 106 at a base that rests on a floor may be approximately 0.4 meters. In one embodiment the elevation system 106 is coupled to the table 104 approximately near a middle of the table 104. The elevation system 106 may use a reduced amount of space with respect to known positioning systems and may allow individuals and imaging equipment to easily maneuver around the positioning system 100.

Figures 2A, 2B, 2C:
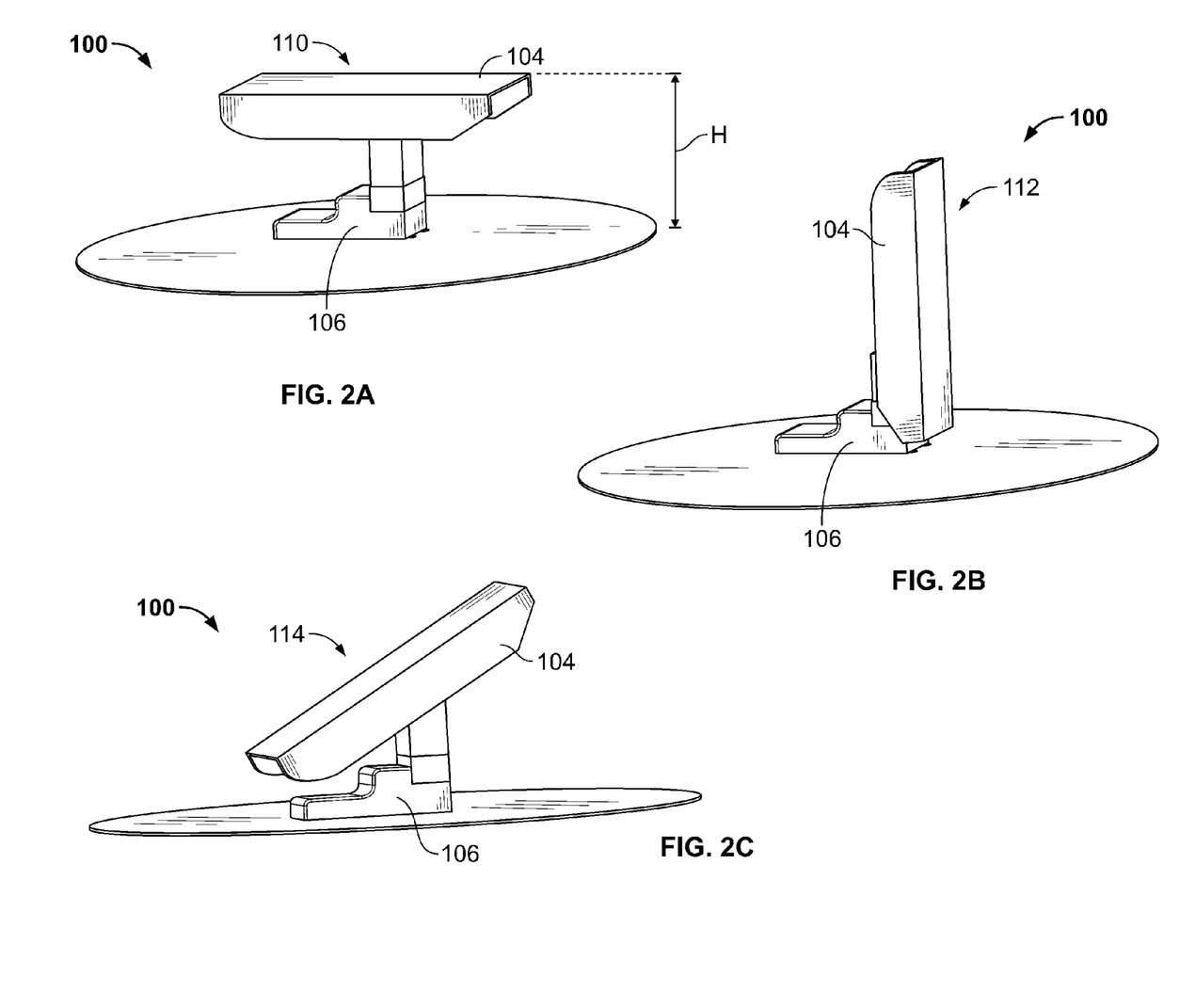
FIG. 2 illustrates perspective side views of the positioning system shown in FIG. 1 when in a fully extended position.

FIG. 2 illustrates perspective side views of the positioning system 100 when the elevation system 106 has moved the table 104 into a fully extended position at a height H. As shown, the table 104 may be rotated from a flat position 110 to a substantially vertical position 112 at approximately 88 degrees with respect to the horizontal axis 192 (FIG. 1) (i.e., Trendelenburg position) or from the flat position 110 to a non-orthogonal position 114 at −30 degrees with respect to the horizontal axis 192 (i.e., Fowler position). The table 104 may also be rotated to any other angle between the positions 112 and 114. In addition, the positioning system 100 may also hold the table 104 in any vertical position between the fully extended and retracted positions and in any rotated position between the Trendelenburg and Fowler positions that is not obstructed by the floor or a piece of equipment. As will be described in further detail, the elevation system 106 is configured to selectively move the table 104 to a desired height between the fully extended position (shown in FIG. 2) and the fully retracted position (shown in FIG. 1).

Figure 3:
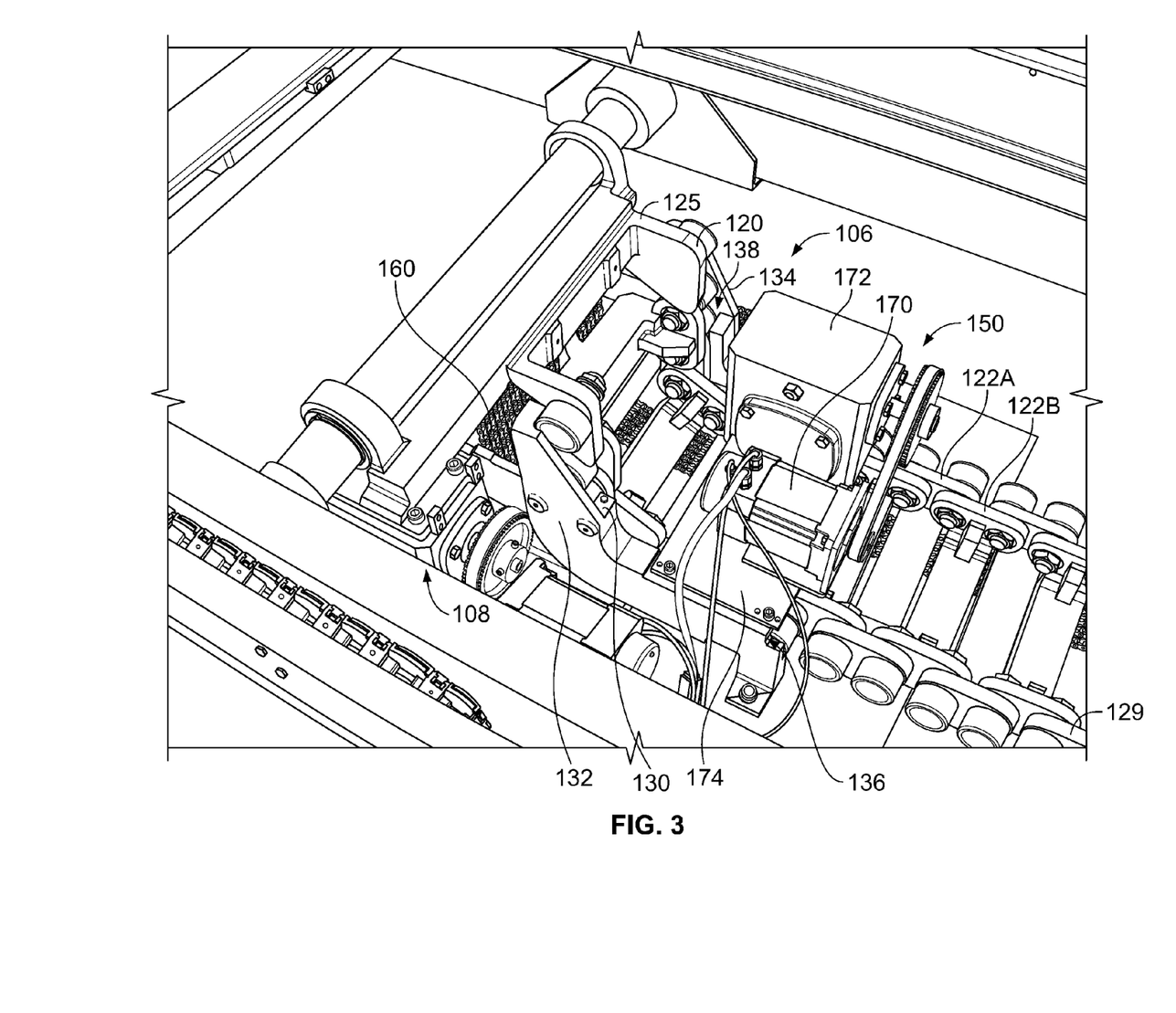
FIG. 3 is an upper perspective view of an elevation system and a rotation system that may be used with the positioning system shown in FIG. 1.
Figure 4:
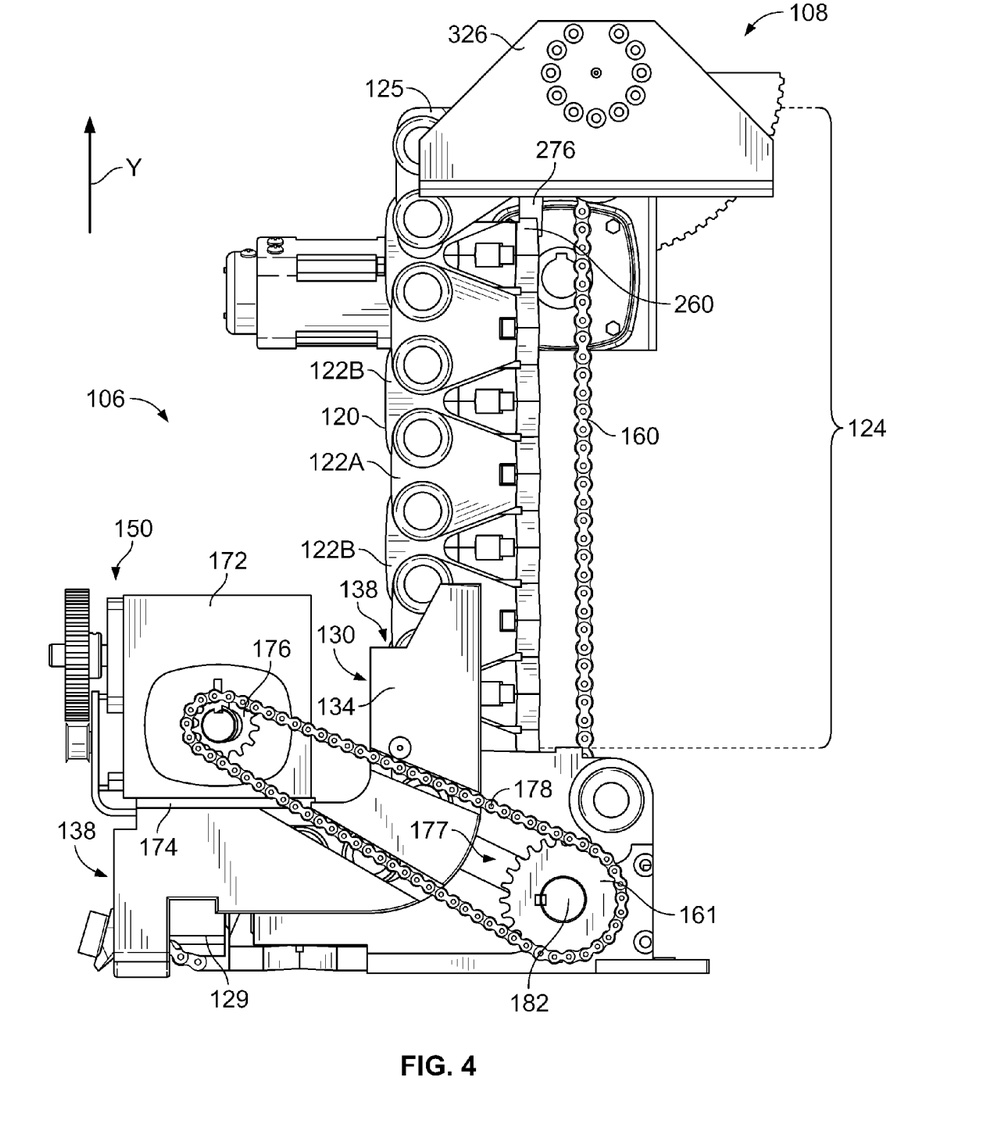
FIG. 4 is a side view of the elevation and rotation systems shown in FIG. 3.

FIGS. 3 and 4 provide further illustration of the elevation system 106 and the rotation system 108. Specifically FIG. 3 shows an upper perspective view of the elevation system 106 and the rotation system 108 while the positioning system 100 (FIG. 1) is in a partially extended position, and FIG. 4 shows a side view of the elevation and rotation systems 106 and 108, respectively, when the positioning system 100 is in a fully extended position. The elevation system 106 includes a flexible column 120 that is operatively coupled to a driving mechanism 150, which moves the column 120 along a guide 130 in order to raise and lower the table 104 (FIG. 1) between the fully retracted position and the fully extended position and any other position therebetween. The column 120 is constructed from a plurality of links 122, 125, and 129 that are coupled to each other in series. Adjacent links, such as links 122A and 122B, are configured to pivot in only one direction from a linear stacked arrangement (shown in FIG. 5) to an obtuse or flexed arrangement (shown in FIG. 8). When the adjacent links 122A and 122B are in the stacked arrangement the links are able to hold and support the table 104 and accompanying load as the table 104 when a lifting force is applied. As such, the column 120 is similar to a "push chain", which includes links in the chain that are unable to flex beyond an 180° angle with respect to each other and are capable of supporting smaller loads. However, as will be discussed in greater detail below, the column 120 is capable of supporting larger loads (e.g., about 400 kg) than conventional push chains.

The guide 130 is configured to receive and redirect the links 122 of the column 120 between the linear stacked arrangement and the flexed arrangement. In the illustrated embodiment, the guide 130 includes a pair of opposing leg supports 132 (FIG. 3) and 134 that include channels 136 and 138 (FIG. 3) formed therein. In the exemplary embodiment, the plurality of links 122 form a rigid lift arm or extension 124 (FIG. 4) that is configured to be coupled to the table 104, a reserve arm or extension 128 (shown in FIG. 9) that includes a portion of the links 122, and an elbow portion 126 (shown in FIG. 9) that connects the lift extension 124 and the reserve extension 128 to each other. As the driving mechanism 150 moves the column 120 to raise the table 104, the links 122 in the elbow portion 126 become part of the lift extension 124 and the leading links in the reserve extension 128 become part of the elbow portion 126. As such, when a lifting force is applied, the table 104 may be moved away from the guide 130 in order to move the individual or object (not shown) into a selected position or to move the individual or object along a predetermined path.

In the illustrated embodiment, the elevation system 106 includes a bias chain assembly 160 that is coupled to the column 120 and is configured to facilitate moving the column and maintaining the lift extension 124 in a rigid stacked arrangement. The chain assembly 160 extends a length of the column 120 and couples to end links 125 and 129. The end link 125 forms the leading end of the column 120 when the table 104 is moved in the load direction Y and the rear link 129 forms the following or back end of the column 120. As will be shown later, the chain assembly 160 may include a plurality of individual chains grouped together. However, the chain assembly 160 may include only one chain in other embodiments. The links of the chain assembly 160 are configured to engage a sprocket assembly 161 (shown in FIG. 8) that includes a plurality of sprockets 162 (shown in FIG. 8) aligned with each other along an axle 182 (FIG. 4). The sprockets 162 include fingers 310 (shown in FIG. 9) that engage openings of the chain assembly 160. The sprocket assembly 161 is operatively coupled to the driving mechanism 150 and is configured to rotate in clockwise and counter-clockwise directions.

When the driving mechanism 150 is operated, the sprockets 162 are rotated causing the chain assembly 160 to move the column 120 along the guide 130. Specifically, when the driving mechanism 150 is operated to raise the table 104, the chain assembly 160 pulls the end link 129 toward the guide 130 causing the links 122 of the column 120 to elongate the lift extension 124 thereby raising the table 104. When the driving mechanism 150 is operated to lower the table, the chain assembly 160 pulls the end link 125 toward the guide 130 causing the links 122 to be removed from the lift extension 124 and added to the reserve extension 128.

Also shown, the driving mechanism 150 includes a motor 170 (FIG. 3) that operates in conjunction with a gearbox 172. Both the motor 170 and the gearbox 172 may rest upon a mounting plate 174 that spans between the supports 132 and 134. As shown in FIG. 4, the gearbox 172 includes a sprocket assembly 176 that is configured to engage a drive chain 178. The drive chain 178 operatively couples the sprocket assembly 176 of the gearbox 172 to a sprocket assembly 177 of the elevation system 106. The sprocket assembly 177 is coupled to the axle 182 that couples to the sprockets 162. When the motor 170 is operated, the sprocket assemblies 176 and 177 are rotated in conjunction with each other causing the axle 182 and attached sprockets 162 to be rotated.

Figure 5:
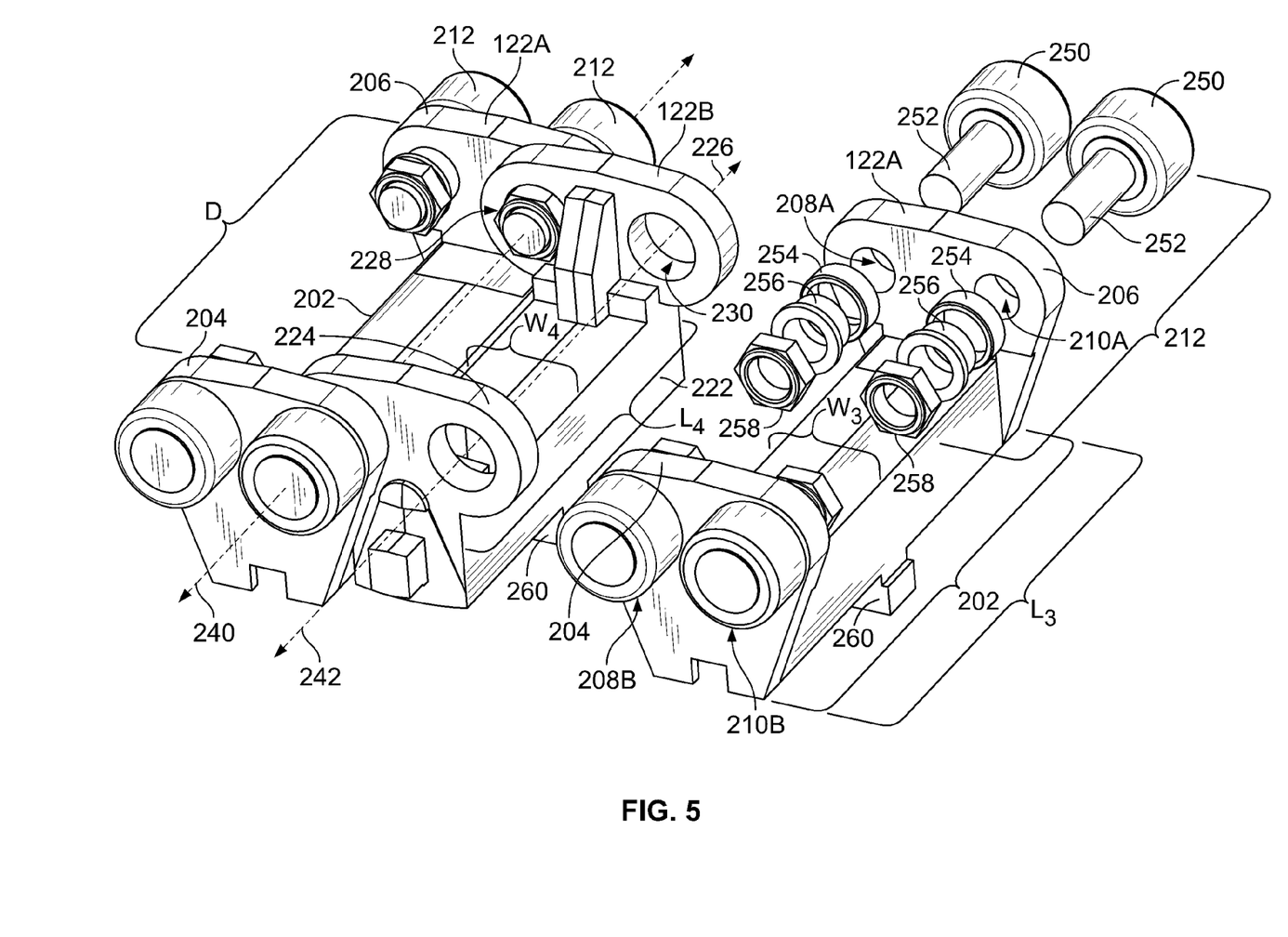
FIG. 5 is an exploded view of the elevation and rotation systems shown in FIG. 3.
Figure 6:
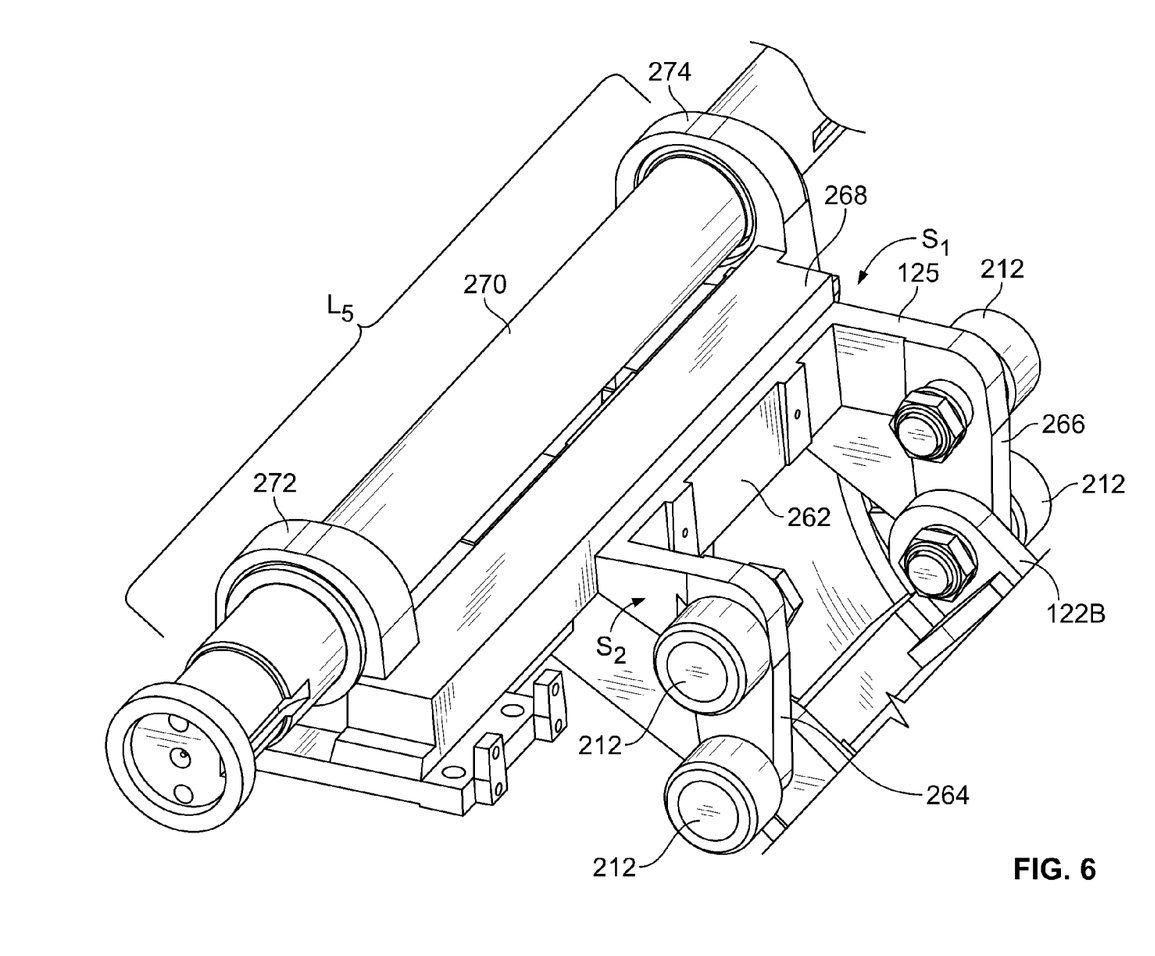
FIG. 6 illustrate links that may be used with the elevation system shown in FIG. 3.
Figure 7:
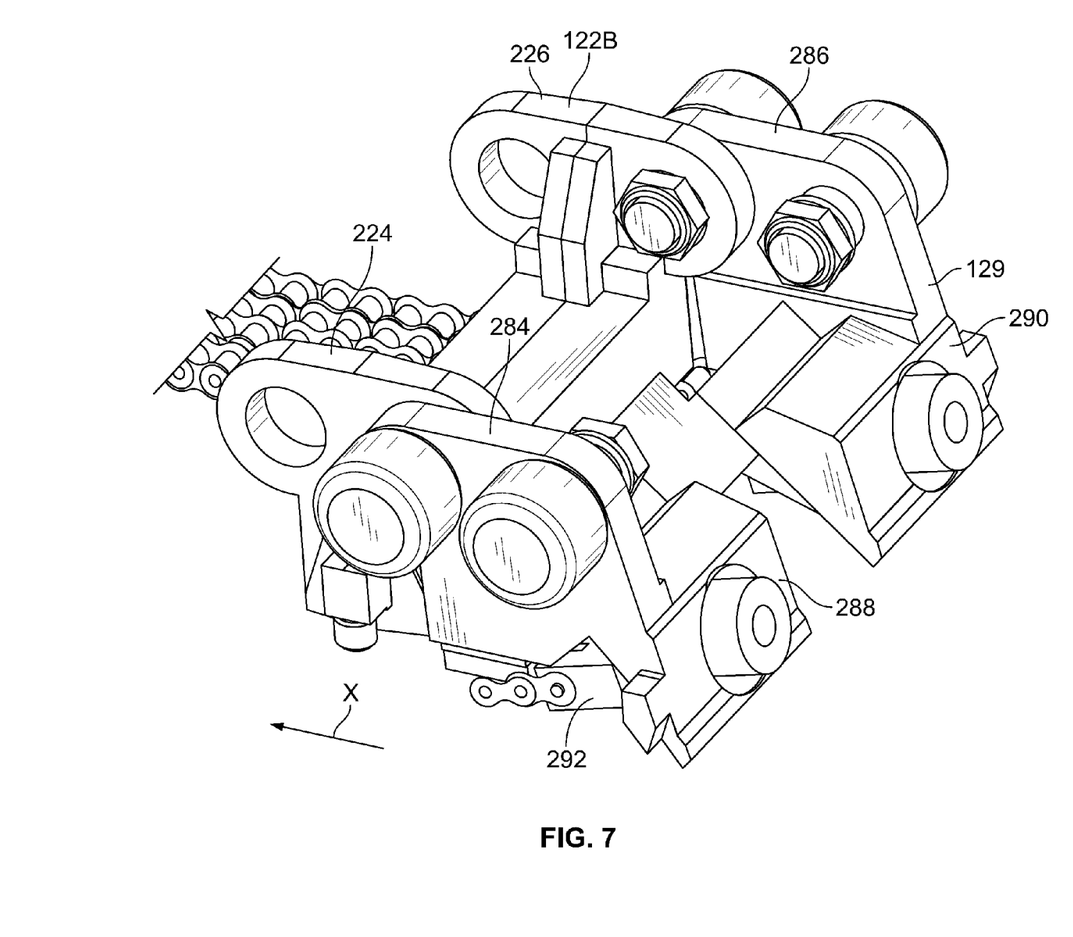
FIG. 7 illustrates another link that may be used with the elevation system shown in FIG. 3.

FIGS. 5-7 illustrate the plurality of links that form the column 120 (FIG. 3) in greater detail. FIG. 5 shows a partially exploded perspective view of adjacent links 122A and 122B. As shown, the column 120 includes alternating links 122A and 122B that are pivotably coupled to one another. Specifically, the link 122A may include a back portion 202 and a pair of opposing arms 204 and 206 that project from opposing ends of the back portion 202. In one embodiment the back portion 202 is substantially rectangular and includes a length $L_3$ and a width $W_3$. The arms 204 and 206 project outward in a perpendicular manner with respect to the back portion 202 and are substantially parallel with respect to each other. Each arm 204 and 206 extends along the width $W_3$ of the back portion 202 and faces the other opposing arm across the length $L_3$. The arms 204 and 206 are spaced apart from each other a distance D that is shorter than the length $L_3$ of the back portion 202. Also shown, each arm 204 and 206 includes a pair of openings 208 and 210 that are configured to receive a roller assembly 212 when the column is fully assembled. As shown, the openings 208A and 210A are aligned with the corresponding openings 208B and 210B, respectively, from the opposing arm.

The link 122B is similarly shaped as the link 122A and includes a back portion 222 and a pair of opposing arms 224 and 226 that each project from an end of the back portion 222. The back portion 202 is substantially rectangular and includes a length $L_4$ and a width $W_4$. The length $L_4$ is shorter than the length $L_3$ of the back portion 202 of the link 122A and is slightly shorter than or substantially equal to the distance D. The arms 224 and 226 project outward in a perpendicular manner with respect to the back portion 222 and are substantially parallel with respect to each other. Each arm 224 and 226 extends along the width $W_4$ of the back portion 222 and faces the other arm across the length $L_4$. The arms 224 and 226 are also spaced apart from each other a distance. Likewise, each arm 224 and 226 includes a pair of openings 228 and 230 that are configured to receive one of the roller assemblies 212 when the column 120 is fully assembled.

To pivotably couple the links 122A and 122B, the links 122A and 122B are placed side-by-side such that the openings 208 and 230 and the openings 210 and 228 are aligned with each other along a fold axis 240 and 242, respectively. More specifically the opening 208 of an arm of one of the links 122A aligns with an adjacent opening 230 of an arm of one of the links 122B and receives one of the roller assemblies 212. Likewise, the opening 210 of an arm of one of the links 122A aligns with an adjacent opening 228 of an arm of one of the links 122B and receives one of the roller assemblies 212. The arms 224 and 226 of the links 122B are positioned between the arms 204 and 206 of the links 122A and may be in slidable contact with each other. For example, the arm 204 would be in slidable contact with the arm 224.

The roller assembly 212 may include includes a cam roller 250 that has a rod 252 configured to be inserted through aligned openings of adjacent arms, such as openings 208 and 230. The roller assembly 212 may also include a bearing 254 configured to engage an inner surface of the corresponding opening, an optional sleeve 256 that is configured to be inserted into the bearing 254, and a nut 258 that engages an end of the rod 252. When the roller assemblies 212 are constructed, and the links 122A and 122B are pivotably coupled to each other, the link 122B may rotate or fold with respect to each adjacent link 122A about the fold axes 240 and 242.

Also shown in FIG. 5, both the links 122A and 122B may include an outer stop projection 260. When adjacent links 122A and 122B are held in the linear stacked arrangement with respect to each other, the stop projections 260 abut each other. As such, the plurality of links 122 (and links 125 and 129) are stacked upon each other forming a rigid back or spine of the column 120 that is capable of supporting large loads. Furthermore, in the linear arrangement, the roller assemblies 212 and arms that extend along each side of the column are aligned with each other. These adjacent roller assemblies 212 and corresponding arms may also form secondary spines that share the load held by the positioning system 100. The links 122A and 122B may also support the table 104 and resist forces applied in a direction along the later axis 194 (FIG. 1).

In alternative embodiments, the links 122A and 122B may each include a plurality of stop projections 260 that about each other. Also, the links 122A and 122B may not have any projections, but the back portions 202 and 222 may be configured to directly abut each other along the lengths $L_3$ and $L_4$, respectively. Furthermore, in one embodiment, the links 122A and 122B are formed from a strong, resilient material capable of supporting large loads as described herein.

FIG. 6 illustrates a perspective view of the end link 125. As shown, the end link 125 includes a back portion 262 and a pair of opposing arms 264 and 266 that each project from an end of the back portion 262. The back portion 262 is directly attached to or integrally formed with a carriage portion 268 that is configured to hold the shaft 270 and the rotation system 108 (FIG. 1). In the illustrated embodiment the carriage portion 268 has a length $L_5$ that extends from one side $S_1$ of the end link 125 to beyond another side $S_2$. The carriage portion 268 includes a pair of grips 272 and 274 that are separated a distance apart from each other and are configured to rotatably hold the shaft 270. The shaft 270, in turn, is configured to support the table 104 (FIG. 1) and the rotation system 108 during operation of the positioning system 100. In the illustrated embodiment the column 120 and the carriage portion 268 are not centered with respect to each other and a majority of the length $L_5$ of the carriage portion 268 is shifted to one side of the positioning system 100. Alternatively, the column 120 and the carriage portion 268 may be centered with respect to each other such that the length $L_5$ of the carriage portion 268 is evenly supported by the column 120.

As shown, the arms 264 and 266 project outward in a perpendicular manner with respect to the back portion 262 and are substantially parallel with respect to each other. Each arm 264 and 266 faces the other arm and is configured to receive a roller assembly 212 and be coupled to the adjacent link 122B as described above with respect to the links 122A and 122B. Also, the end link 125 includes a stop projection 276 (shown in FIG. 4) that engages a stop projection 260 of the adjacent link 122B.

FIG. 7 is a perspective view of the end link 129 coupled to one of the links 122B. The end link 129 may include arms 284 and 286 that are configured to couple to arms 224 and 226, respectively, of an adjacent link 122B as described above. The end link 129 may also include a pair of rear guards 288 and 290 that are positioned at the end of the column 120. FIG. 7 illustrates a portion of the chain assembly 160 being coupled to one of the rear guards 288 via an anchor 292. When the driving mechanism 150 (FIG. 2) is in operation, the chain assembly 160 pulls the end link 129 and the links 122 of the rear extension 128 in a non-load direction (indicated as an arrow labeled X). The force or tension in the chain assembly 160 may facilitate maintaining the rear extension 128 of the links 122 and 129 in the linear arrangement. The rear guards 288 and 290 may prevent the links 122 from moving along the guide 130 (FIG. 3) thereby stopping the movement of the column 120.

Figure 8:
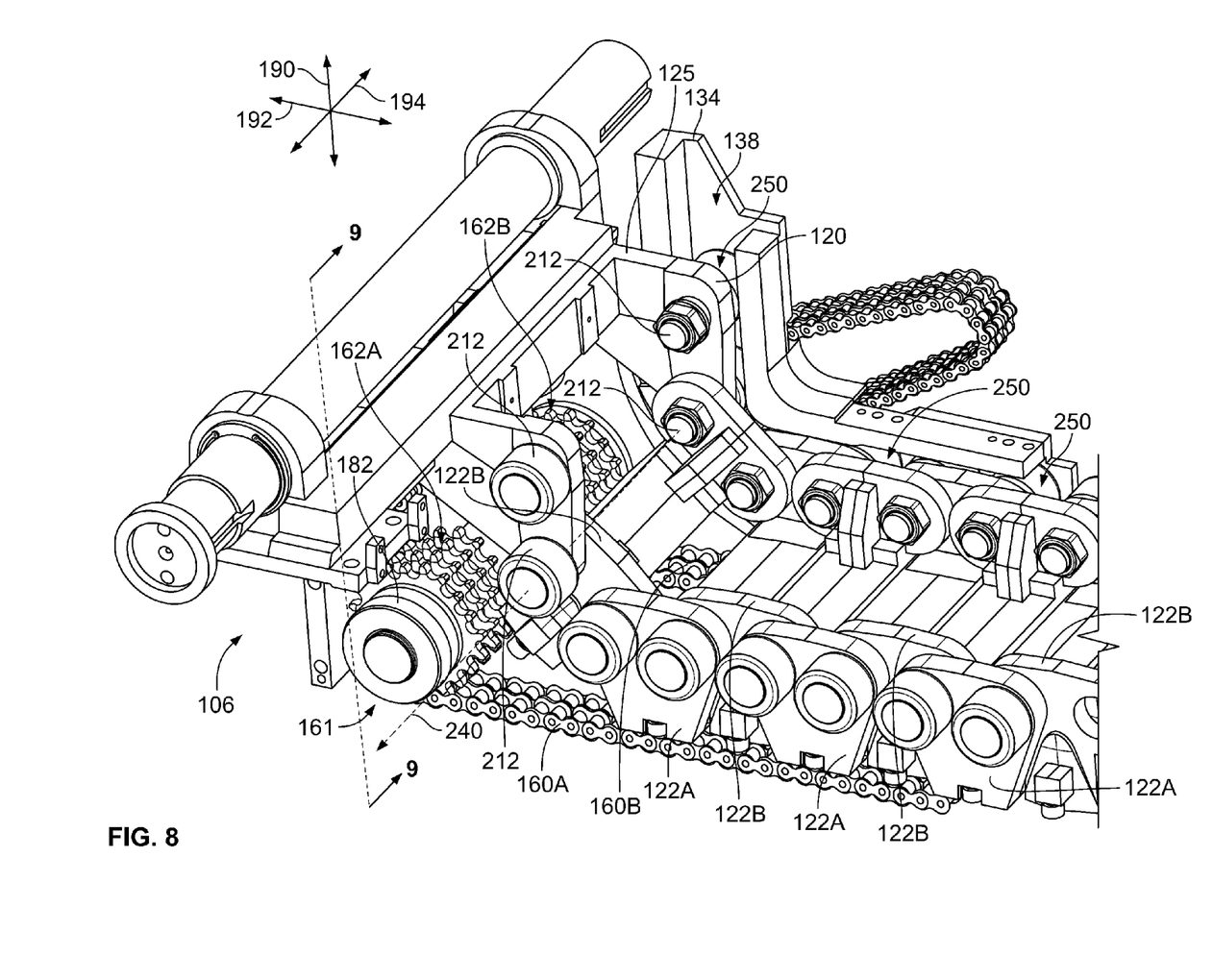
FIG. 8 is a partial perspective view of the elevation system shown in FIG. 3.
Figure 9:
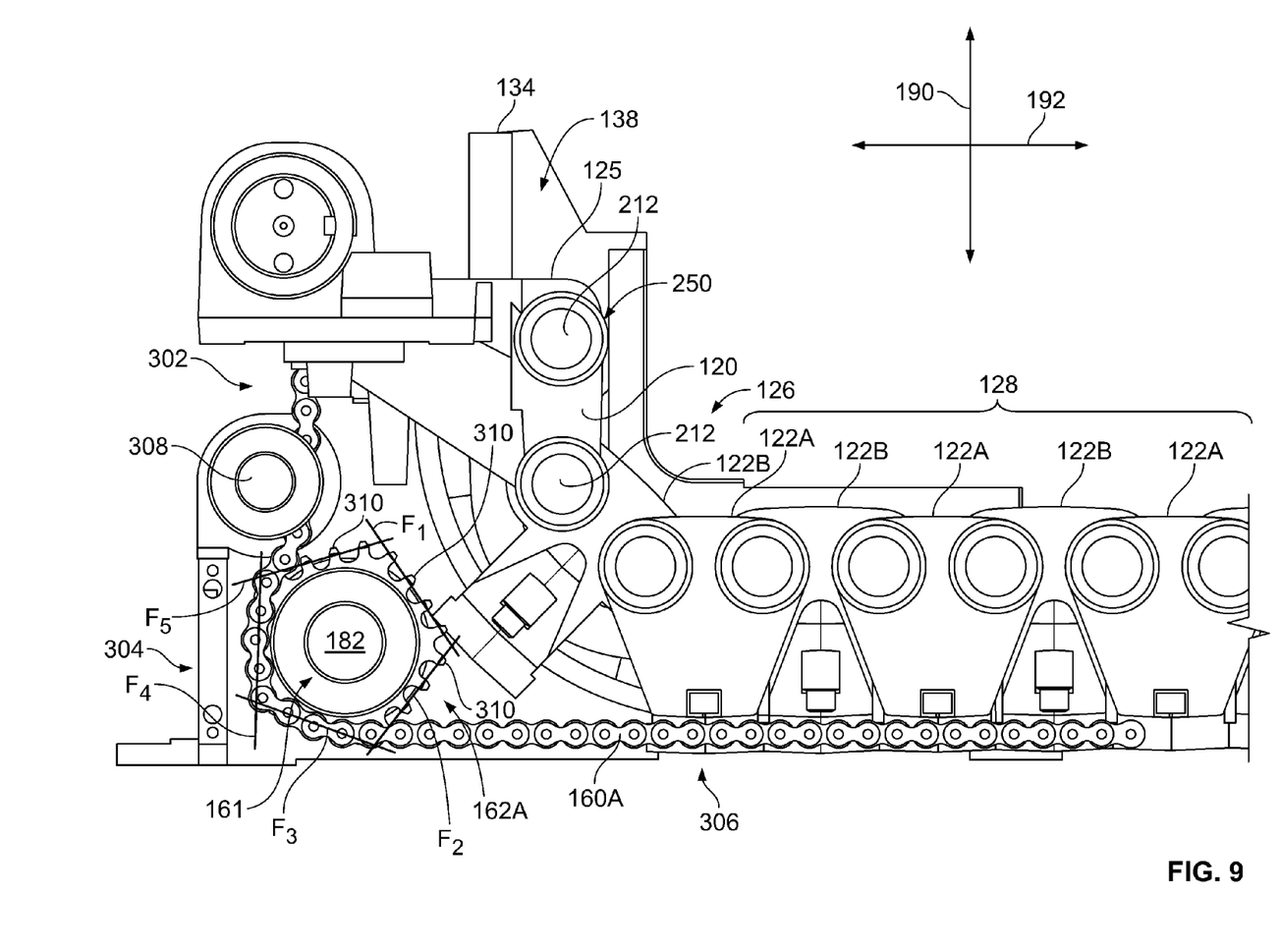
FIG. 9 is a side view of the elevation system shown in FIG. 8 taken along the line 9-9.

FIGS. 8 and 9 illustrate the interaction between the column 120 and other components of the elevation system 106 (FIG. 3). Specifically, FIG. 8 is a partial perspective view of the elevation system 106 when the column 120 is in the fully retracted position. FIG. 9 is a side view of the elevation system 106 shown in FIG. 8 taken along the line 9-9. Although FIGS. 8 and 9 only illustrate one support 134 of the guide 130 (FIG. 3), the following description with respect to the support 134 may similarly be applied to the support 132. As shown, in the fully retracted position, the roller assemblies 212 of the end link 125 are held within the channel 138 of the support 134. As described above, the end link 125 and the adjacent link 122B are pivotably coupled to each other via the roller assemblies 212. When the column 120 is in the fully retracted position, the end link 125 and the adjacent link 122B form an obtuse or flexed arrangement with respect to each other about the corresponding fold axis 240 (FIG. 8). As can be seen, the end link 125 is upright and substantially parallel to the vertical axis 190 and forms the lift extension 124 (FIG. 4). The link 122B that is adjacent to the end link 125 is non-orthogonal with respect to the vertical axis 190 and to the horizontal axis 192 and forms the elbow portion 126 (FIG. 9). The subsequent links 122 of the column 120 are substantially parallel to the horizontal axis 192 and form the reserve extension 128 (FIG. 9).

As the lift extension 124 of the column 120 is moved in the load direction, the links 122 are moved along the guide 130. As used herein, the phrase "moved along" includes any portion of the column 120 moving (e.g., sliding, rolling, translating) along any surface of the guide 130. The column 120 may continuously contact or intermittently touch the surface of the guide 130 as the column 120 moves along. In the exemplary embodiment the roller assemblies 212 of the corresponding links 122 move through the channel 138 and are redirected by the path of the channel 138. However, in alternative embodiments, the guide 130 may not have channels, but may have other features for directing the links 122. For example, the guide 130 may include rails where a portion of the column 120 grips the rails as the links 122 extend along the rails.

As the links 122 move along the guide 130, the links 122 of the reserve extension 128 may contact inner walls of the channel 138. More specifically the cam rollers 250 coupled to the links 122 move along the channel 138 and are directed by the channel walls. When the link 122 that is positioned within the elbow portion 126 of the channel 138 begins to pivot back into the linear arrangement with respect to the leading adjacent link, the stop projections 260 of the two links contact each other and form a part of the spine of the lift extension 124. As each subsequent link 122 is redirected by the guide 130, the stop projection 260 of the subsequent link moves into a linear arrangement with respect to the preceding link. As such, as the column 120 is moved along the guide 130, additional links 122 become a part of the lift extension 124 thereby adding to the length or height of the lift extension 124. Furthermore, as links 122 are added to the lift extension 124, links 122 are removed from the reserve extension 128. Thus, when the elevation system 106 is in operation, some of the links 122 may be stored within the reserve extension 128. The positioning system 100 utilizes these stored links 122 and redirects the links 122 in order to add height to the lift extension 124.

In the exemplary embodiment, the reserve extension 128 extends in a direction substantially parallel to the horizontal axis 192. However, the reserve extension 128 may extend in other directions and the links 122 of the reserve extension 128 are not required to be in the linear arrangement. For example, the reserve extension 128 may include one or more folds so that the reserve extension 128 does not use as much space or area in the horizontal direction.

FIGS. 8 and 9 also illustrate the sprocket assembly 161 and the chain assembly 160. As shown, the sprocket assembly 161 includes the plurality of sprockets 162A and 162B (both shown in FIG. 8), which are operatively coupled to the axle 182. Each sprocket 162A is configured to engage one of the chains of the chain assembly 160A (FIG. 8), and each sprocket 162B is configured to engage one of the chains of the chain assembly 160B (FIG. 8). As discussed above, when the driving mechanism 150 is operated, the axle 182 is rotated in the selected direction causing the chain assemblies 160 to move the column 130 in the selected direction.

As shown in FIG. 9, in the exemplary embodiment, the chain assembly 160A extends between and connects the end links 125 and 129 (FIG. 7). Although the following description is specifically applied to the chain assembly 160A and sprockets 162A, the description may similarly be applied to the chain assembly 160B and the sprockets 162B. The chain assembly 160A includes a lift portion 302, an elbow portion 304, and a rear portion 306. In some embodiments, as the links 122 of the column 120 are moved along the guide 130, tension in the chain is varies due to a net variation caused by movement of the column 120 with respect to the chain assembly 160A. As such, the chain assembly 160A and the elevation system 106 may be configured to create a tension that facilitates maintaining the links of the column 120 in a linear arrangement.

For example, as shown in FIG. 9, the chain assembly 160A may interact with the sprocket assembly 161 and an idler shaft 308 in order to create tension within the chain assembly 160A. More specifically the idler shaft 308 and the axle 182 of the sprocket assembly 161 may extend between and through the pair of supports 132 (FIG. 3) and 134. The sprockets 162A of the sprocket assembly 161 include fingers 310 that are configured to engage the chain assembly 160A. In the illustrated embodiment the fingers 310 are not evenly distributed around a center of the sprocket 162A and do not project radially outward therefrom. Rather, some of the fingers 310 are aligned with each other to form a side of the sprocket 162A. FIG. 9 shows the sprocket 162A being substantially polygonal and having five sides $F_1$-$F_5$ formed by groups of fingers 310. Each side $F_1$-$F_5$ includes four fingers 310 substantially aligned with each other and forming a slight bulge or curvature of the corresponding side.

The idler shaft 308 is positioned near the sprocket 162A such that the links of the chain assembly 160A that extend between the sprocket 162A and the idler shaft 308 form an angle less than 90°. In the illustrated embodiment, the angle formed by the links of the chain assembly 160 is about 72°+/−5°. But other angles may be formed if, for example, the position or the distance between the idler shaft 308 and the sprocket 162A is changed or if the sprocket 162A has more or less sides of fingers 310.

However, other mechanisms may be used in order to account for the net variation caused by movement of the column 120 with respect to the chain assembly 160. For example, a spring mechanism may be coupled to the anchor 292 (FIG. 7) in order to maintain tension within the chain assembly 160. Furthermore, the positioning system 100 may still function without a mechanism to account for the net variation.

Figure 10:
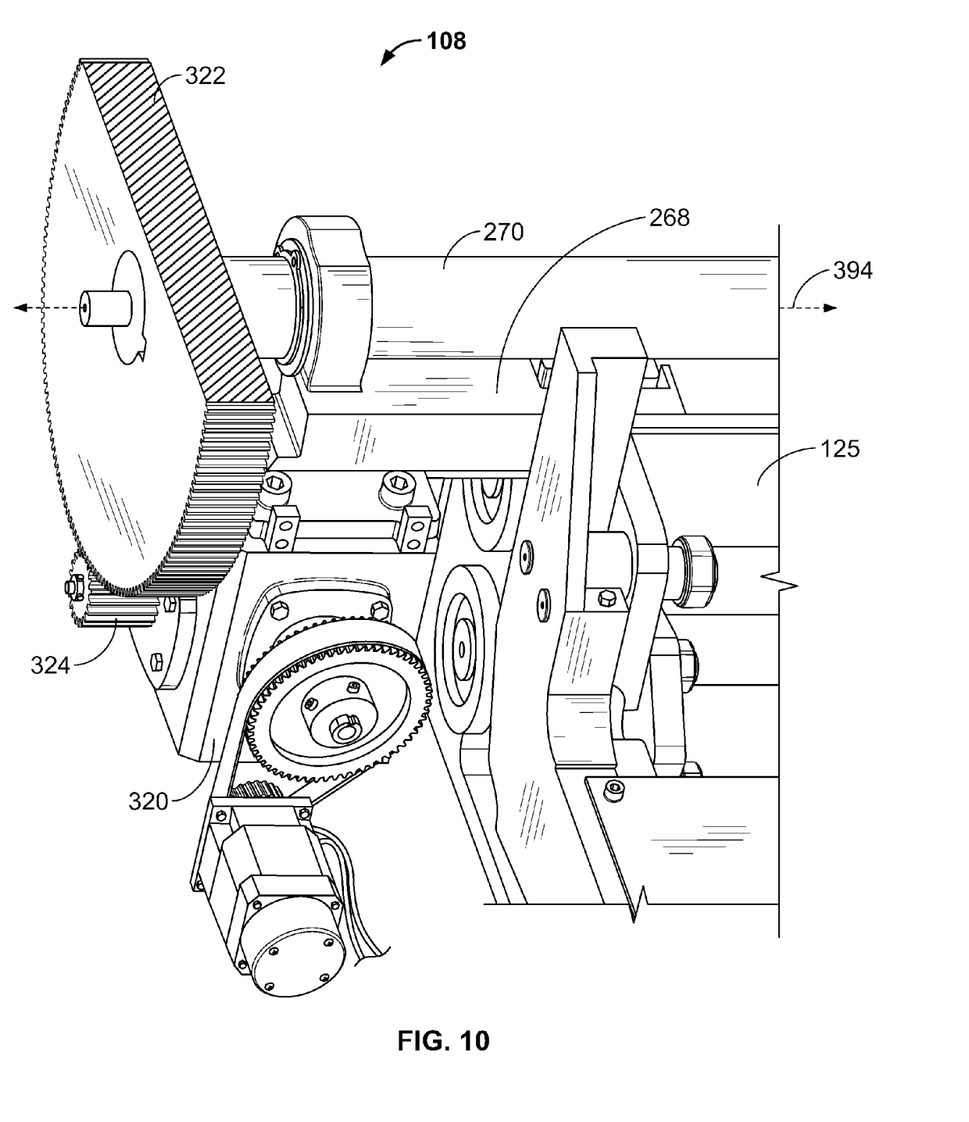
FIG. 10 is a perspective view of the rotation system shown in FIG. 3.

FIG. 10 shows a perspective view of a portion of the rotation system 108. The rotation system 108 includes a gearbox 320 that attaches to the carriage portion 268 of the end link 125, a sector gear 322 that is attached to the shaft 270 and operatively coupled to the support 102 or table 104 (FIG. 1), and a pinion 324 that is operatively coupled to the gearbox 320 and the gear 322. Also, the shaft 270 may be operatively coupled to a support grip 326 (shown in FIG. 4) that grips the support 102 and facilitates rotating the support 102 when the shaft 270 is rotated. When operated, the gearbox 320 moves the pinion 324 causing the sector gear 322 to rotate. As such, the support 102 or table 104 may be rotated about a rotation axis 394 that extends through the shaft 270 and substantially parallel to the axis 194 (FIG. 1). Because the rotation system 108 is coupled to the end link 125, the rotation system 108 may be operated at any position between the fully retracted and fully extended positions.

In some alternative embodiments, the positioning system 100 includes a plurality of elevations systems 106 that operate in conjunction with each other to move the support 102. For example, two elevation systems 106 may be positioned to face each other. The columns 120 may share an end link 125 or the end links 125 may be coupled together and only one rotation system 108 may be used. Because the links 122 of each column 120 may only flex in one direction and because these directions oppose each other, the elevation systems 106 may operate without bias chain assemblies 160.

Furthermore, other embodiments may use alternative driving mechanisms 150. For example, a motor may include a sprocket assembly or gear assembly that directly engages the links 122 of the column 120. In addition, the column 120 may be moved manually via a ratchet system or the column may be moved through a hydraulic system.

In another alternative embodiment, the end link 125 may attach to a side of the support 102. In such an embodiment, the rotation system 106 may be configured to rotate the support 102 a full 360°.

A method for moving a patient into position or in a guided manner is also provided. The method includes coupling a column to a table that is configured to hold the patient. The column is configured to support and move the table when a lifting force is applied. The column also includes a plurality of links that are pivotably coupled to each other in series. The adjacent links are configured to pivot in only one direction from a linear stacked arrangement. The method also includes moving the column along a guide configured to receive and direct the links of the column. The guide is configured to direct the links into the linear stacked arrangement when the links are moved by the lifting force.

A method for moving a support into position or in a guided manner is also provided. The method includes coupling the support to an end of a flexible column. The column includes a plurality of links coupled to one another. The links form a linear lift extension and a reserve extension. The lift extension is configured to support the table and extend in a load direction, and the reserve extension has at least a portion that extends in a non-load direction. The method also includes coupling the support to a rotation system that is configured to rotate the support about a rotation axis proximate to the end of the column. The method further includes moving the column along a guide configured to receive the links as the column is moved in the load direction. The guide redirects the links such that links received from the reserve extension are added to the lift extension.

One technical effect that may be provided by the embodiments described herein includes greater movement capabilities. For instance, a table or support may be moved a greater distance than known positioning systems. Also, the rotation system may rotate the support further than known positioning systems because the column uses little space. Another technical effect includes greater load capacities than known positioning systems. Furthermore, the positioning systems described herein may provide a substantially constant mechanical advantage as the table or support is being moved.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A positioning system for moving a patient into position or in a guided manner, the system comprising:
   a table configured to hold the patient;
   a flexible column coupled to the table and configured to support and move the table, the column comprising a plurality of links pivotably coupled to one another in series, wherein adjacent links are configured to pivot between a linear stacked arrangement and a flexed arrangement, the links forming a lift extension that supports the table when the links are in the linear stacked arrangement; and
   a guide configured to receive and redirect the links of the column into the linear stacked arrangement when the links are moved by a lifting force thereby adding the links to the lift extension, the table moving away from the guide as the links are added to the lift extension.

2. The positioning system in accordance with claim 1 further comprising a driving mechanism operatively coupled to the column and configured to move the column along the guide.

3. The positioning system in accordance with claim 1 further comprising a rotation system coupled to the table and the column, the rotation system configured to rotate the table about a rotation axis, the rotation axis moving with the table and away from the guide as the links are added to the lift extension.

4. The positioning system in accordance with claim 3 wherein the table has a length and a width, the rotation axis proximate to a middle of the length and extending along the width of the table.

5. The positioning system in accordance with claim 1 wherein the links include an end link that has a fixed position with respect to the table, the end link moving away from the guide as the links are added to the lift extension.

6. The positioning system in accordance with claim 1 wherein adjacent links are coupled to one another along a fold axis and are configured to rotate about the fold axis between the linear stacked arrangement and a flexed arrangement.

7. The positioning system in accordance with claim 1 wherein the adjacent links include respective back portions that engage each other and prevent the adjacent links from pivoting beyond the linear stacked arrangement, the back portions of the links in the lift extension supporting a load of the table.

8. The positioning system in accordance with claim 1 wherein the table is selectively movable in a vertical direction between a first height and a greater second height when the table is in a substantially horizontal orientation.

9. The positioning system in accordance with claim 7 wherein the back portions include respective stop projections, the stop projections of the adjacent links contacting and abutting each other in the lift extension to support the load of the table.

10. A positioning system for moving a patient into position or in a guided manner, the system comprising:
    a table configured to hold the patient;
    a flexible column coupled to the table and configured to support and move the table, the column comprising a plurality of links pivotably coupled to one another in series, wherein adjacent links are configured to pivot in only one direction from a linear stacked arrangement; and
    a guide configured to receive and redirect the links of the column into the linear stacked arrangement when the links are moved by a lifting force, wherein the positioning system further comprises a bias chain coupled to the links, the bias chain being configured to maintain the links of the column in the linear stacked arrangement when the column is not being redirected by the guide.

11. A method for moving a patient into position or in a guided manner, the method comprising:
    coupling a table, configured to hold the patient, to a flexible column that is configured to support and move the table when a lifting force is applied, the column including a plurality of links pivotably coupled to one another in series, wherein adjacent links are configured to pivot between a linear stacked arrangement and a flexed arrangement, the links forming a lift extension that supports the table when the links are in the linear stacked arrangement; and
    moving the column along a guide configured to receive and redirect the links of the column, the guide configured to direct the links into the linear stacked arrangement when the links are moved by the lifting force thereby adding the links to the lift extension, the table moving away from the guide as the links are added to the lift extension.

12. The method in accordance with claim 11 further comprising operatively coupling a driving mechanism to the column, the driving mechanism being configured to move the column along the guide.

13. The method in accordance with claim 11 wherein the column includes adjacent links coupled to one another along a fold axis, the method further comprising configuring the adjacent links to rotate about the fold axis between the linear stacked arrangement and a flexed arrangement.

14. The method in accordance with claim 11 further comprising coupling a bias chain to the links and configuring the bias chain to maintain the links of the lift extension in the linear stacked arrangement.

15. The method in accordance with claim 11 further comprising a coupling a rotation system to the table and to the column, the rotation system being configured to rotate the table about a rotation axis.

16. The method in accordance with claim 1 wherein the links include an end link that has a fixed position with respect to the table, the end link moving away from the guide as the links are added to the lift extension.

17. A method for moving a support into position or in a guided manner, the method comprising:

coupling the support to an end of a flexible column, the column including a plurality of links pivotably coupled to one another in series, the links forming an adjustable linear lift extension and a reserve extension, the lift extension being configured to support the table and extending in a load direction and the reserve extension having at least a portion that extends in a non-load direction;

coupling the support to a rotation system configured to rotate the support about a rotation axis proximate to the end of the column; and moving the column along a guide configured to receive the links as the column is moved in the load direction, the guide redirecting the links such that links received from the reserve extension are added to the lift extension, the rotation axis moving with the support when the links are added to the lift extension.

18. The method in accordance with claim 17 further comprising operatively coupling a driving mechanism to the column and configuring the driving mechanism to move the column along the guide.

19. The method in accordance with claim 17 wherein moving the column along the guide includes moving the column such that the column provides a substantially constant mechanical advantage.

20. The method in accordance with claim 17 further comprising coupling a bias chain to the links and configuring the bias chain to maintain the links of the lift extension in the linear stacked arrangement.

* * * * *